US009849132B2

(12) United States Patent
Hendrick et al.

(10) Patent No.: US 9,849,132 B2
(45) Date of Patent: Dec. 26, 2017

(54) PRODUCTS AND PHARMACEUTICAL COMPOSITIONS

(71) Applicant: Intra-Cellular Therapies, Inc., New York, NY (US)

(72) Inventors: Joseph Hendrick, Bridgeport, CT (US); Jennifer O'Brien, New York, NY (US); Gretchen Snyder, New York, NY (US); Peng Li, New Milford, NJ (US); Lawrence P. Wennogle, Hillsborough, NJ (US)

(73) Assignee: INTRA-CELLULAR THERAPIES, INC., New York, NY (US)

( * ) Notice: Subject to any disclaimer, the term of this patent is extended or adjusted under 35 U.S.C. 154(b) by 0 days.

(21) Appl. No.: 15/110,640

(22) PCT Filed: Jan. 8, 2015

(86) PCT No.: PCT/US2015/010697
§ 371 (c)(1),
(2) Date: Jul. 8, 2016

(87) PCT Pub. No.: WO2015/106032
PCT Pub. Date: Jul. 16, 2015

(65) Prior Publication Data
US 2016/0324860 A1 Nov. 10, 2016

Related U.S. Application Data

(60) Provisional application No. 61/925,015, filed on Jan. 8, 2014.

(51) Int. Cl.
| A61K 31/519 | (2006.01) |
| A61K 31/53 | (2006.01) |
| A61K 45/06 | (2006.01) |
| C07D 487/04 | (2006.01) |
| C07D 487/14 | (2006.01) |
| A61K 9/00 | (2006.01) |

(52) U.S. Cl.
CPC .......... *A61K 31/519* (2013.01); *A61K 9/0048* (2013.01); *A61K 31/53* (2013.01); *A61K 45/06* (2013.01); *C07D 487/04* (2013.01); *C07D 487/14* (2013.01)

(58) Field of Classification Search
None
See application file for complete search history.

(56) References Cited

U.S. PATENT DOCUMENTS

| 5,294,612 A | 3/1994 | Bacon et al. |
| 5,393,755 A | 2/1995 | Neustadt et al. |
| 5,824,683 A | 10/1998 | McKittrick et al. |
| 5,939,419 A | 8/1999 | Tulshian et al. |
| 6,013,621 A | 1/2000 | Nishi et al. |
| 6,492,371 B2 | 12/2002 | Roylance et al. |
| 6,756,373 B1 | 6/2004 | Allerton et al. |
| 6,969,719 B2 | 11/2005 | Asberom et al. |
| 7,153,824 B2 | 12/2006 | Palmer et al. |
| 8,273,750 B2 | 9/2012 | Li et al. |
| 8,273,751 B2 | 9/2012 | Li et al. |
| 8,536,159 B2 | 9/2013 | Li et al. |
| 8,633,180 B2 | 1/2014 | Li et al. |
| 8,664,207 B2 | 3/2014 | Li et al. |
| 8,697,710 B2 | 4/2014 | Li et al. |
| 8,829,008 B2 | 9/2014 | Li et al. |
| 8,846,693 B2 | 9/2014 | Li et al. |
| 8,859,564 B2 | 10/2014 | Li et al. |
| 8,927,556 B2 | 1/2015 | Li et al. |
| 9,000,001 B2 | 4/2015 | Li et al. |
| 9,006,258 B2 | 4/2015 | Fienberg et al. |
| 9,073,936 B2 | 7/2015 | Li et al. |
| 9,157,906 B2 | 10/2015 | Greengard et al. |
| 9,198,924 B2 | 12/2015 | Mates et al. |
| 9,255,099 B2 | 2/2016 | Li et al. |
| 9,403,836 B2 | 8/2016 | Li et al. |
| 9,468,637 B2 | 10/2016 | Fienberg et al. |
| 9,556,186 B2 | 1/2017 | Li et al. |
| 9,598,426 B2 | 3/2017 | Li et al. |
| 9,624,230 B2 | 4/2017 | Li et al. |
| 2002/0198377 A1 | 12/2002 | Niewohner et al. |
| 2003/0162782 A1 | 8/2003 | Grossman et al. |
| 2005/0075795 A1 | 4/2005 | Pandit et al. |
| 2007/0208029 A1 | 9/2007 | Barlow et al. |
| 2008/0176961 A1 | 7/2008 | Greengard et al. |
| 2008/0193964 A1 | 8/2008 | Greengard et al. |
| 2008/0194592 A1 | 8/2008 | Mates et al. |

(Continued)

FOREIGN PATENT DOCUMENTS

| DE | 19931206 | 1/2001 |
| EP | 0201188 | 12/1986 |

(Continued)

OTHER PUBLICATIONS

Ahlstrom et al., "Inactivation of Atrial Natriuretic Factor-Stimulated Cyclic Guanosine 39,59-Monophosphate (cGMP) in UMR-106 Osteoblast-like Cells", Biochemical Pharmacology, vol. 59, p. 1133-1139, (2000).

Boess et al., "Inhibition of phosphodiesterase 2 increases neuronal cGMP, synaptic plasticity and memory performance", Neuropharmacology, vol. 47, p. 1081-1092, (2004).

Brandon et al., "Potential CNS Applications for Phosphodiesterase Enzyme Inhibitors", Annual Reports in Medicinal Chemistry, vol. 42, p. 1-10, 2007.

Domek-Łopacińska et al., "The effect of selective inhibition of cyclic GMP hydrolyzing phosphodiesterases 2 and 5 on learning and memory processes and nitric oxide synthase activity in brain during aging", Brain Research, vol. 1216, p. 68-77, (2008).

(Continued)

*Primary Examiner* — Samantha Shterengarts
(74) *Attorney, Agent, or Firm* — Hoxie & Associates LLC

(57) ABSTRACT

The present invention relates to a product comprising a PDE1 inhibitor and a PDE2 inhibitor, in free or salt form, pharmaceutical compositions comprising them and their use as pharmaceuticals for the treatment of cAMP and/or cGMP related disorders.

10 Claims, 1 Drawing Sheet

(56) References Cited

U.S. PATENT DOCUMENTS

| | | |
|---|---|---|
| 2011/0009322 A1 | 1/2011 | Sharif et al. |
| 2011/0312978 A1 | 12/2011 | Davis et al. |
| 2013/0018063 A1 | 1/2013 | Li et al. |
| 2014/0005155 A1 | 1/2014 | Li et al. |
| 2014/0011783 A1 | 1/2014 | Li et al. |
| 2014/0148421 A1 | 5/2014 | Li et al. |
| 2014/0194396 A1 | 7/2014 | Li et al. |

FOREIGN PATENT DOCUMENTS

| | | |
|---|---|---|
| EP | 0911333 | 4/1999 |
| JP | 5068857 | 3/2011 |
| KR | 10-1991-0006866 | 9/1991 |
| WO | WO 91/19717 | 12/1991 |
| WO | WO 94/19351 | 9/1994 |
| WO | WO 98/46606 | 10/1998 |
| WO | WO 98/52568 | 11/1998 |
| WO | WO 03/002567 | 1/2003 |
| WO | WO 03/020702 | 3/2003 |
| WO | WO 03/020724 | 3/2003 |
| WO | WO 03/042216 | 5/2003 |
| WO | WO 2006/133261 | 12/2006 |
| WO | WO 2007/143705 | 12/2007 |
| WO | WO 2009/073210 | 6/2009 |
| WO | WO 2010/062366 | 6/2010 |
| WO | WO 2011/043816 | 4/2011 |
| WO | WO 2011/153129 | 12/2011 |
| WO | WO 2011/153135 | 12/2011 |
| WO | WO 2011/153136 | 12/2011 |
| WO | WO 2011/153138 | 12/2011 |
| WO | WO 2013/192556 | 12/2013 |
| WO | WO 2014/151409 | 9/2014 |

OTHER PUBLICATIONS

Suvarna et al., "Hydrolysis of N-Methyl-D-aspartate Receptor-Stimulated cAMP and cGMP by PDE4 and PDE2 Phosphodiesterases in Primary Neuronal Cultures of Rat Cerebral Cortex and Hippocampus", The Journal of Pharmacology and Experimental Therapeutics, vol. 302(1), p. 249-256, (2002).
Van Staveren et al., The effects of phosphodiesterase inhibition on cyclic GMP and cyclic AMP accumulation in the hippocampus of the rat, Brain Research, vol. 888, p. 275-286, (2001).
Velardez et al., "Role of phosphodiesterase and protein kinase G on nitric oxide-induced inhibition of prolactin release from the rat anterior pituitary", European Journal of Endocrinology, vol. 143, p. 279-284, (2000).
Wakabayashi et al., "Involvement of Phosphodiesterase Isozymes in Osteoblastic Differentiation", vol. 17(2), p. 249-256, (2002).
International Search Report of International Application No. PCT/US2015/010697 dated Apr. 6, 2015, 2 pages.
Masood et al., "Reversal of Oxidative Stress-Induced Anxiety by Inhibition of Phosphodiesterase-2 in Mice", The Journal of Pharmacology and Experimental Therapeutics, vol. 326(2), p. 369-379, (2008).
Masood et al., "Anxiolytic Effects of Phosphodiesterase-2 Inhibitors Associated with Increased cGMP Signaling", The Journal of Pharmacology and Experimental Therapeutics, vol. 331(2), p. 690-699, (2009).
Reierson et al., "Repeated antidepressant therapy increases cyclic GMP signaling in rat hippocampus", Neuroscience Letters, vol. 466(3), p. 149-153, (2009).
Ahn, H. et al., "Potent Tetracyclic Guanine Inhibitors of PDE1 and PDE5 Cyclic Guanosine Monophosphate Phosphodiesterases with Oral Antihypertensive Activity," J. Med. Chem., 1997, 40(14), 2196-2210.
Aswar, "Anti-Cataleptic Activity of Various Extracts of Ocimum Sanctum," International Journal of Pharma. Research and Development, 2010, 2(6), 1-7.
Banker, G.S. et al., Modern Pharmaceutics, Marcel Dekker, New York, 1996.

Bender, A.T. et al., "Cyclic Nucleotide Phosphodiesterases: Molecular Regulation to Clinical Use," Pharmcol. Rev., 2006, 58, 488-520.
Boyd, et al. "Dopamine receptor signaling and current and future antipsychotic drugs," Handbook Exp Pharmacol., 2012, 212, 53-86.
Chalimoniuk, "Upregulation of guanylyl cyclase expression and activity in striatum of MPTP-induced parkinsonism in mice," Biochem. Biophys. Res. Commun., 2004, 324(1), 118-126.
Deshmukh, et al., "Amelioration of intracerebroventricular streptozotocin induced cognitive dysfunction and oxidative stress by vinpocetine-a PDE1 inhibitor," European Journal of Pharmacology, 2009, 620(1-3), 49-56.
Dewald, H.A. et al., "Synthesis and Potential Antipsychotic Activity of 1 H-Imidazo[1,2-c]pyrazolo[3,4-e]pyrimidines," J. Med. Chem., 1988, 31, 454-461.
Ehrman et al., "Phosphodiesterase 1B differentially modulates the effects of methamphetamine on locomotor activity and spatial learning through DARPP32-dependent pathways: evidence from PDE1B-DARPP32 double-knockout mice," Genes Brain Behav., 2006, 5(7), 540-551.
Fienberg, A.A. et al., "DARPP-32: Regulator of the Efficacy of Dopaminergic Neurotransmission," Science, 1998, 281, 838-842.
Filgueiras, et al., "Phosphodiesterase type 1 inhibition improves learning in rats exposed to alcohol during the third trimester equivalent of human gestation," Neuroscience Letters, 2010, 473(3), 202-207.
Greengard, P. et al., "Beyond the Dopamine Receptor: the DARPP-32/Protein Phosphatase-1 Cascade," Neuron, 1999, 23, 435-447.
Han, P. et al., "The Calcium/Calmodulin-dependent Phosphodiesterase PDE1C Down-regulates Glucose-induced Insulin Secretion," J. Bio. Chem., 1999, 274(32), 22337-22344.
Hulley, et al., "Cyclic AMP promotes the survival of dopaminergic neurons in vitro and protects them from the toxic effects of MPP+," J. Neural Transm. Suppl., 1995, 46, 217-228.
Jiang, M. et al., "Chemoenzymatic Asymmetric Total Synthesis of Phosphodiesterase Inhibitors: Preparation of a Polycyclic Pyrazolo[3,4-d]pyrimidine from an Acylnitroso Diels-Alder Cycloadduct-Derived Aminocyclopentenol," J. Org. Chem., 2005, 70, 2824-2827.
Kakkar, et al., "Amantadine: an antiparkinsonian agent inhibits bovine brain 60 kDa calmodulin-dependent cyclic nucleotide phosphodiesterase isozyme," Brain Res., 1997, 749(2), 290-294.
Kakkar, et al., "Calmodulin-dependent cyclic nucleotide phosphodiesterase (PDE1)," Cell Mol. Life Sci., 1999, 55(8-9), 1164-86.
Kakkar, et al., "Inhibition of Bovine Brain Calmodulin-Dependent Cyclic Nucleotide Phosphodiesterase Isozymes by Deprenyl," Life Sciences, 1996, 59(21), 337341.
Klaissle, "Physical activity and environmental enrichment regulate the generation of neural precursors in the adult mouse substantia nigra in a dopamine-dependent manner," BMC Neurosci., 2012, 31, 13-132.
Kleppisch, "Phosphodiesterases in the central nervous system," Handb Exp Pharmacol., 2009, 191, 71-92.
Laddha, et al., "A new therapeutic approach in Parkinson's disease: Some novel quinazoline derivatives as dual selective phosphodiesterase 1 inhibitors and anti-inflammatory agents," Bioorganic & Medicinal Chemistry, 2009, 17(19), 6796-6802.
Mani, S.K. et al., "Requirement for DARPP-32 in Progesterone-Facilitated Sexual Receptivity in Female Rats and Mice," Science, 2000, 287, 1053.
Medina, "Therapeutic Utility of Phosphodiesterase Type 1 Inhibitors in Neurological Conditions," Front. Neurosci., 2011, 5(21), 6.
Murray, F. et al., "Expression and activity of cAMP phosphodiesterase isoforms in pulmonary artery smooth muscle cells from patients with pulmonary hypertension: role for PDE1," Am. J. Physiol. Lung Cell Mol. Physiol., 2007, 292, L294-L303.
Nishi, A. et al., "Advanced Research on Dopamine Signaling to Develop Drugs for the Treatment of Mental Disorders: Biochemical and Behavioral Profiles of Phosphodiesterase Inhibition in Dopaminergic Neurotransmission," J. Pharmacol. Sci., 2010, 114, 6-16.

(56) References Cited

OTHER PUBLICATIONS

Polli, J.W. et al., "Expression of a Calmodulin-Dependent Phosphodiesterase Isoform (PDE1B1) Correlates With Brain Regions Having Extensive Dopaminergic Innervation," 1994, The Journal of Neuroscience, 14, 1251-1261.
Reed, T.M. et al., "Phosphodiesterase 1B Knock-Out Mice Exhibit Exaggerated Locomotor Hyperactivity and DARPP-32 Phosphorylation in Response to Dopamine Agonists and Display Impaired Spatial Learning," The Journal of Neuroscience, 2002, 22(12), 5188-5197.
Rybalkin, S.D. et al., "Cyclic GMP Phosphodiesterases and Regulation of Smooth Muscle Function," Circ. Res., 2003, 93, 280-291.
Schmidt, "Phosphodiesterase inhibitors as potential cognition enhancing agents," Current Topics in Medicinal Chemistry, 2010, 10(2), 222-230.
Sharma, et al., "Regulation of Calmodulin-Stimulated Cyclic Nucleotide Phosphodiesterase (PDE1): Review," International Journal of Molecular Medicine, 2006, 18, 95-105.
Shimizu, K. et al., "Calmodulin-Dependent Cyclic Nucleotide Phosphodiesterase (PDE1) is a Pharmacological Target of Differentiation-Inducing Factor-1, an Antitumor Agent Isolated from Dictyostelium," Cancer Research, 2004, 64, 2568-2571.
Shook, et al., "Design and Characterization of Optimized Adenoside A2A/A1 Receptor Antagonists for the Treatment of Parkinson's Disease," J. Med. Chem., 2012, 1-47.
Vatter, S. et al., "Differential Phosphodiesterase Expression and Cytosolic Ca in Human CNS Tumour Cells and in Non-Malignant and Malignant Cells of Rat Origin," J. of Neurochemistry, 2005, 93, 321-329.
Wolff, M.E., Burger's Medicinal Chemistry and Drug Discovery, Fifth Ed., vol. 1: Principles and Practice, John Wiley & Sons, 1995, 975.
Xia, Y. et al., "Synthesis and Evaluation of Polycyclic Pyrazolo[34-d]pyrimidines as PDE1 and PDE5 cGMP Phosphodiesterase Inhibitors," J. Med. Chem., 1997, 40, 4372-4377.

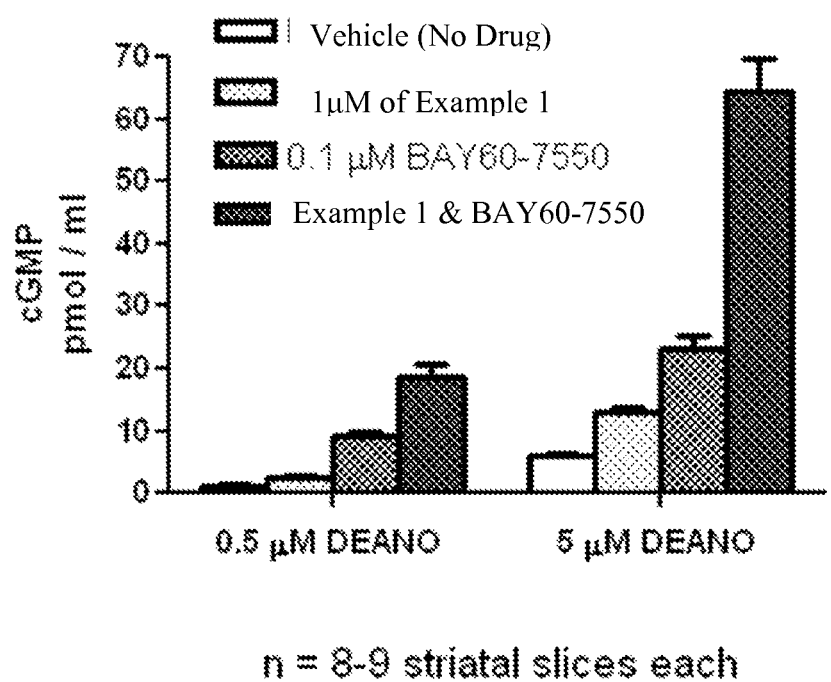

PRODUCTS AND PHARMACEUTICAL COMPOSITIONS

CROSS-REFERENCE TO RELATED APPLICATIONS

This application is a U.S. National Stage application of PCT/US2015/010697, filed on Jan. 8, 2015, which claims priority to U.S. Provisional Application No. 61/925,015 filed Jan. 8, 2014, the contents of which are hereby incorporated by reference in their entirety.

TECHNICAL FIELD

The present invention relates to a product comprising a PDE1 inhibitor and a PDE2 inhibitor, in free or salt form, pharmaceutical compositions comprising the same in free or pharmaceutically acceptable salt form, and their use as pharmaceuticals for the treatment of cAMP and/or cGMP related disorders.

BACKGROUND OF THE INVENTION

Eleven families of phosphodiesterases (PDEs) have been identified but only PDEs in Family I, the $Ca^{2+}$-calmodulin-dependent phosphodiesterases (CaM-PDEs), have been shown to mediate both the calcium and cyclic nucleotide (e.g. cAMP and cGMP) signaling pathways. The three known CaM-PDE genes, PDE1A, PDE1B, and PDE1C, are all expressed in central nervous system tissue. PDE is expressed throughout the brain with higher levels of expression in the CA1 to CA3 layers of the hippocampus and cerebellum and at a low level in the striatum. PDE1A is also expressed in the lung and heart. PDE1B is predominately expressed in the striatum, dentate gyrus, olfactory tract and cerebellum, and its expression correlates with brain regions having high levels of dopaminergic innervation. Although PDE1B is primarily expressed in the central nervous system, it may be detected in the heart. PDE1C is primarily expressed in olfactory epithelium, cerebellar granule cells, and striatum. PDE is also expressed in the heart and vascular smooth muscle.

Cyclic nucleotide phosphodiesterases decrease intracellular cAMP and cGMP signaling by hydrolyzing these cyclic nucleotides to their respective inactive 5'-monophosphates (5'AMP and 5'GMP). CaM-PDEs play a critical role in mediating signal transduction in brain cells, particularly within an area of the brain known as the basal ganglia or striatum. For example, NMDA-type glutamate receptor activation and/or dopamine D2 receptor activation result in increased intracellular calcium concentrations, leading to activation of effectors such as calmodulin-dependent kinase II (CaMKII) and calcineurin and to activation of CaM-PDEs, resulting in reduced cAMP and cGMP. Dopamine D1 receptor activation, on the other hand, leads to activation of nucleotide cyclases, resulting in increased cAMP and cGMP. These cyclic nucleotides in turn activate protein kinase A (PKA; cAMP-dependent protein kinase) and/or protein kinase G (PKG; cGMP-dependent protein kinase) that phosphorylate downstream signal transduction pathway elements such as DARPP-32 (dopamine and cAMP-regulated phosphoprotein) and cAMP responsive element binding protein (CREB). Phosphorylated DARPP-32 in turn inhibits the activity of protein phosphatase-1 (PP-1), thereby increasing the state of phosphorylation of substrate proteins such as progesterone receptor (PR), leading to induction of physiologic responses. Studies in rodents have suggested that inducing cAMP and cGMP synthesis through activation of dopamine D1 or progesterone receptor enhances progesterone signaling associated with various physiological responses, including the lordosis response associated with receptivity to mating in some rodents. See Mani, et al., Science (2000) 287: 1053, the contents of which are incorporated herein by reference.

CaM-PDEs can therefore affect dopamine-regulated and other intracellular signaling pathways in the basal ganglia (striatum), including but not limited to nitric oxide, noradrenergic, neurotensin, CCK, VIP, serotonin, glutamate (e.g., NMDA receptor, AMPA receptor), GABA, acetylcholine, adenosine (e.g., A2A receptor), cannabinoid receptor, natriuretic peptide (e.g., ANP, BNP, CNP), DARPP-32, and endorphin intracellular signaling pathways.

Phosphodiesterase (PDE) activity, in particular, phosphodiesterase 1 (PDE1) activity, functions in brain tissue as a regulator of locomotor activity and learning and memory. PDE1 is a therapeutic target for regulation of intracellular signaling pathways, preferably in the nervous system, including but not limited to a dopamine D1 receptor, dopamine D2 receptor, nitric oxide, noradrenergic, neurotensin, CCK, VIP, serotonin, glutamate (e.g., NMDA receptor, AMPA receptor), GABA, acetylcholine, adenosine (e.g., A2A receptor), cannabinoid receptor, natriuretic peptide (e.g., ANP, BNP, CNP), endorphin intracellular signaling pathway and progesterone signaling pathway. For example, inhibition of PDE1B should act to potentiate the effect of a dopamine D1 agonist by protecting cGMP and cAMP from degradation, and should similarly inhibit dopamine D2 receptor signaling pathways, by inhibiting PDE1 activity. Chronic elevation in intracellular calcium levels is linked to cell death in numerous disorders, particularly in neurodegenerative diseases such as Alzheimer's, Parkinson's and Huntington's Diseases and in disorders of the circulatory system leading to stroke and myocardial infarction. PDE1 inhibitors are therefore potentially useful in diseases characterized by reduced dopamine D1 receptor signaling activity, such as Parkinson's disease, restless leg syndrome, depression, narcolepsy and cognitive impairment. PDE1 inhibitors are also useful in diseases that may be alleviated by the enhancement of progesterone-signaling such as female sexual dysfunction.

PDE2 also hydrolyzes both cAMP and cGMP with a high Vmax and low Km. The enzyme is allosterically stimulated by cGMP binding to one of its GAF domains. Only one gene family, PDE2A, codes for the PDE2 with three splice variants of PDE2, namely PDE2A1, PDE2A2 and PDE2A3. PDE2A1 is localized in the cytosol while PDE2A2 and PDE2A3 are membrane bound. PDE2 has been shown to have therapeutic potential in neuronal development, learning and memory. Van Staveren et al., *Brain Res.* (2001) 888:275; O'Donnell et al., *J. Pharm. Exp. Ther.* (2002) 302:249; Velardez et al., *Eur. J. Endo.* (2000) 143:279; Gallo-Paget et al., *Endo.* (1999) 140:3594; Allardt-Lamberg et al., *Biochem. Pharm.* (2000) 59:1133; and Wakabayashi et al., *Miner. Res.* (2002) 17:249. Inhibition of PDE2A demonstrates enhanced cognitive function across multiple preclinical models of cognitive performance that reflects improvements in recognition memory, social interaction and working memory, which are all deficient in schizophrenia. Boess et al., *Neuropharmacology* (2004) 47(7):1081-92. PDE2A inhibition also improves cognitive deficits that develop in aging and Alzheimer's disease. Domek-Lopacinska et al., *Brain Res.* (2008) 1216:68-77; Brandon et al., *Annual Reports in Medicinal Chemistry* (2007) 42:4-5. PDE2A inhibition has also been demonstrated to show efficacy in preclinical models of anxiety and depression. Masood et al., *JPET* (2009) 331(2):690-699; Masood et al., *JPET* (2008) 326(2):369-379; Reierson et al., *Neurosci. Lett.* (2009) 466(3):149-53.

PDE1 and PDE2 have been shown to be useful therapeutic targets. There is thus a need for a product that comprises a compound that selectively inhibits PDE1 activity and a compound that selectively inhibits PDE2 activity, in free or salt form.

SUMMARY OF THE INVENTION

Nitric oxide stimulates soluble guanylyl cyclase (GC) to increase the levels of cGMP. Cyclic nucleotide phosphodiesterases decrease intracellular cAMP and cGMP signaling by hydrolyzing these cyclic nucleotides to their respective inactive 5'-monophosphates (5'AMP and 5'GMP).

Our scientists have discovered that when inhibition of both PDE1 and PDE2 is achieved, this combination has more than additive effect on the nitric oxide signaling in the brain, thereby increasing nitric oxide stimulated cGMP levels in the brain. Therefore, in the first aspect, the invention provides a product comprising a PDE1 inhibitor and a PDE2 inhibitor, in free or pharmaceutically acceptable salt form. For example, provided is a product comprising (a) a PDE1 inhibitor, in free or pharmaceutically acceptable salt form, and (b) a PDE2 inhibitor, in free or pharmaceutically acceptable salt form.

In the second aspect, the invention provides a pharmaceutical composition comprising a PDE1 inhibitor and a PDE2 inhibitor as described herein, in free or pharmaceutically acceptable salt form, in admixture with a pharmaceutically acceptable diluent or carrier (Pharmaceutical Composition I). The PDE1 inhibitor and PDE2 inhibitor may be in a fixed pharmaceutical composition (wherein the PDE1 and PDE2 therapeutic agents are in a single dosage form) or as a free pharmaceutical composition (wherein the PDE1 and PDE2 therapeutic agents are in a separate dosage form). For example, provided is a pharmaceutical composition comprising:
 (a) a PDE1 inhibitor, in free or pharmaceutically acceptable salt form, and
 (b) a PDE2 inhibitor, in free or pharmaceutically acceptable salt from, in admixture with a pharmaceutically acceptable carrier or diluent. In a particular embodiment of the second aspect, the invention further provides a pharmaceutical composition for topical ophthalmic use comprising a PDE1 inhibitor and a PDE2 inhibitor; for example an ophthalmic solution, suspension, cream or ointment comprising a PDE1 inhibitor and a PDE2 inhibitor of the invention, in free or ophthalmologically acceptable salt form, in combination or association with an ophthalmologically acceptable diluent or carrier.

PDE1 and PDE2 inhibitors are known in the art. In a particular embodiment of the invention, a PDE1 inhibitor of the current invention includes those disclosed in WO 2006/133261, WO 2007/143705, WO 2008/063505, WO 2008/070095, WO 2009/075784, WO 2009/073210, WO 2010/065153, WO 2010/065148, WO 2010/065151, WO 2010/065149, WO 2010/065147, WO 2010/065152, WO 2010/098839, WO 2010/132127, WO 2011/153129, WO 2011/153135, WO 2011/153136, WO 2011/153138, WO 2012/171016, the contents of each of which are incorporated by reference in their entirety. In another particular embodiment, the PDE1 inhibitor is (6aR,9aS)-5,6a,7,8,9,9a-hexahydro-5-methyl-3-(phenylamino)-2-((4-Pyridin-2yl)-benzyl)-cyclopent[4,5]imidazo[1,2-a]pyrazolo[4,3-e]pyrimidin-4(2H)-one, in free or salt form. In another particular embodiment, the PDE1 inhibitor is (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one, in free or salt form.

In another particular embodiment, a PDE2 inhibitor of the current invention includes those disclosed in WO 2010/054260, WO 2010/054253, WO 2012/104293, WO 2013/000924, WO 2013/034755, WO 2013/034758, WO 2013/034761, WO 2006/072615, WO 2006/024640, WO 2006/072612, WO 2012/114222, WO 2012/168817, WO 2005/041957, WO 2005/061497, WO 2011/011312, EP 1749824, EP 1548011, EP 1556055, U.S. Pat. No. 4,766,122, WO 2002/068423, WO 2002/050078, WO 2002/009713, WO 98/32755, U.S. Pat. No. 5,861,396, WO 2004/089953, U.S. Pat. No. 5,861,396 and U.S. Pat. No. 6,573,263. In a particular embodiment, the PDE2 inhibitor of the invention is 2-(3,4-Dimethoxybenzyl)-7-{(1R)-1-[(1R)-1-hydroxyethyl]-4-phenylbutyl}-5-methylimidazo[5,1-f][1,2,4]triazin-4(3H)-one (BAY 60-7550), in free or salt form.

In the third aspect, the invention provides a method of using the product of the invention. The products of the invention are useful in the treatment of diseases characterized by disruption of or damage to cAMP and cGMP mediated pathways, e.g., as a result of increased expression of PDE1 or PDE2 or decreased expression of cAMP and cGMP due to inhibition or reduced levels of inducers of cyclic nucleotide synthesis, such as dopamine and nitric oxide (NO). By preventing the degradation of cAMP and cGMP by PDE1 and PDE2, thereby increasing intracellular levels of cAMP and cGMP, particularly cGMP, the products and pharmaceutical compositions of the invention potentiate the activity of cyclic nucleotide synthesis inducers. Therefore, the invention provides methods of treatment of any one or more of the following conditions:
 (i) Neurodegenerative diseases, including Parkinson's disease, restless leg tremors, dyskinesias, Huntington's disease, Alzheimer's disease, and drug-induced movement disorders;
 (ii) Mental disorders, including depression, attention deficit disorder, attention deficit hyperactivity disorder, bipolar illness, anxiety, sleep disorders, e.g., narcolepsy, cognitive impairment, dementia, Tourette's syndrome, autism, fragile X syndrome, psychostimulant withdrawal, and drug addiction;
 (iii) Circulatory and cardiovascular disorders, including cerebrovascular disease, stroke, congestive heart disease, hypertension, pulmonary hypertension, pulmonary arterial hypertension, and sexual dysfunction;
 (iv) Respiratory and inflammatory disorders, including asthma, chronic obstructive pulmonary disease, and allergic rhinitis, as well as autoimmune and inflammatory diseases;
 (v) Any disease or condition characterized by low levels of cAMP and/or cGMP (or inhibition of cAMP and/or cGMP signaling pathways) in cells expressing PDE1 or PDE2; and/or
 (vi) Any disease or condition characterized by reduced dopamine D1 receptor signaling activity,
comprising administering to a human or animal patient in need thereof an effective amount of the Pharmaceutical Composition I of the invention which comprises a PDE1 inhibitor and a PDE2 inhibitor, in free or pharmaceutically acceptable salt form as described herein, in admixture with a pharmaceutically acceptable diluents or carrier.

The Pharmaceutical Composition I may be administered as a fixed pharmaceutical composition (wherein the PDE1 and PDE2 therapeutic agents are in a single dosage form) or as a free pharmaceutical composition (wherein the PDE1 and PDE2 therapeutic agents are in a separate dosage form).

In one embodiment, the invention provides methods of treatment or prophylaxis for narcolepsy. In this embodiment, Pharmaceutical Composition I may be used as the only therapeutic agent, but may also be used in combination or for co-administration with other active agents. Thus, the invention further comprises a method of treating narcolepsy comprising administering, e.g., simultaneously, sequentially, or contemporaneously administering, therapeutically effective amounts of
  (i) Pharmaceutical Composition I, and
  (ii) a compound to promote wakefulness or regulate sleep, e.g., selected from (a) central nervous system stimulants-amphetamines and amphetamine like compounds, e.g., methylphenidate, dextroamphetamine, methamphetamine, and pemoline; (b) modafinil, (c) antidepressants, e.g., tricyclics (including imipramine, desipramine, clomipramine, and protriptyline) and selective serotonin reuptake inhibitors (including fluoxetine and sertraline); and/or (d) gamma hydroxybutyrate (GHB),
in free or pharmaceutically acceptable salt form, to a human or animal patient in need thereof. The Pharmaceutical Composition I may be used as the only therapeutic agent (e.g., in a fixed or free pharmaceutical composition) or use in combination for co-administration with another active agent.

In another embodiment, the invention further provides methods of treatment or prophylaxis of a condition which may be alleviated by the enhancement of progesterone signaling comprising administering an effective amount of the Pharmaceutical Composition I of the invention, to a human or animal patient in need thereof. Diseases or conditions that may be ameliorated by enhancement of progesterone signaling include, but are not limited to, female sexual dysfunction, secondary amenorrhea (e.g., exercise amenorrhoea), anovulation, menopause, menopausal symptoms, hypothyroidism, pre-menstrual syndrome, premature labor, infertility, for example infertility due to repeated miscarriage, irregular menstrual cycles, abnormal uterine bleeding, osteoporosis, autoimmmune disease, multiple sclerosis, prostate enlargement, prostate cancer, and hypothyroidism. For example, by enhancing progesterone signaling, the PDE1 and PDE2 inhibitors may be used to encourage egg implantation through effects on the lining of uterus, and to help maintain pregnancy in women who are prone to miscarriage due to immune response to pregnancy or low progesterone function. The PDE1 and PDE2 inhibitors as described herein may also be useful to enhance the effectiveness of hormone replacement therapy, e.g., administered in combination with estrogen/estradiol/estriol and/or progesterone/progestins in postmenopausal women, and estrogen-induced endometrial hyperplasia and carcinoma. The methods of the invention are also useful for animal breeding, for example to induce sexual receptivity and/or estrus in a nonhuman female mammal to be bred.

In this embodiment, PDE1 and PDE2 Inhibitors may be used in the foregoing methods of treatment or prophylaxis as the only therapeutic agents, but may also be used in combination or for co-administration with other active agents, for example in conjunction with hormone replacement therapy. Thus, the invention further comprises a method of treating disorders that may be ameliorated by enhancement of progesterone signaling comprising administering, e.g., simultaneously, sequentially, or contemporaneously administering, therapeutically effective amounts of
  (i) the Pharmaceutical Composition I of the invention, and
  (ii) a hormone, e.g., selected from estrogen and estrogen analogues (e.g., estradiol, estriol, estradiol esters) and progesterone and progesterone analogues (e.g., progestins), in free or pharmaceutically acceptable salt form, to a human or animal patient in need thereof.

The invention also provides a method for enhancing or potentiating dopamine D1 intracellular signaling activity in a cell or tissue comprising contacting said cell or tissue with an amount of a PDE1 inhibitor and a PDE2 inhibitor, sufficient to inhibit PDE1 and PDE2 activity.

The invention also provides a method for treating a PDE1 and/or PDE2-related disorder, a dopamine D1 receptor intracellular signaling pathway disorder, or disorders that may be alleviated by the enhancement of the progesterone signaling pathway in a patient in need thereof comprising administering to the patient an effective amount of the Pharmaceutical Composition I of the invention, wherein PDE1 and PDE2 activity modulates phosphorylation of DARPP-32 and/or the GluR1 AMPA receptor.

In another aspect, the invention also provides a method for the treatment for glaucoma or elevated intraocular pressure comprising topical administration of a therapeutically effective amount of the Pharmaceutical Composition I of the invention, in an ophthalmically compatible carrier to the eye of a patient in need thereof. However, treatment may also include a systemic therapy. Systemic therapy includes treatment that can directly reach the bloodstream, or oral methods of administration, for example.

Optionally, the pharmaceutical composition comprising the PDE1 inhibitor and the PDE2 inhibitor may be administered sequentially or simultaneously with a third drug useful for treatment of glaucoma or elevated intraocular pressure. Where the pharmaceutical composition comprising the PDE1 inhibitor and the PDE2 inhibitor are administered with other agents, the therapeutically effective amount of the third or subsequent agent may be below the amount needed for activity as monotherapy. Accordingly, a subthreshold amount (i.e., an amount below the level necessary for efficacy as monotherapy) may be considered therapeutically effective and also may also be referred alternatively as an effective amount. Indeed, an advantage of administering different agents with different mechanisms of action and different side effect profiles may be to reduce the dosage and side effects of either or both agents, as well as to enhance or potentiate their activity as monotherapy.

The invention thus provides the method of treatment of a condition selected from glaucoma and elevated intraocular pressure comprising administering to a patient in need thereof an effective amount, e.g., a subthreshold amount, of an agent known to lower intraocular pressure concomitantly, simultaneously or sequentially with an effective amount, e.g., a subthreshold amount, of a PDE1 inhibitor and a PDE2 inhibitor of the invention, in free or pharmaceutically acceptable salt form, such that amount of the agent known to lower intraocular pressure and the amount of the PDE1 inhibitor and PDE2 inhibitor in combination are effective to treat the condition.

In one embodiment, one or both of the agents are administered topically to the eye. Thus the invention provides a method of reducing the side effects of treatment of glaucoma or elevated intraocular pressure by administering a reduced dose of an agent known to lower intraocular pressure concomitantly, simultaneously or sequentially with an effective amount of a PDE1 inhibitor. However, methods other than topical administration, such as systemic therapeutic administration, may also be utilized.

The optional additional agent or agents for use in combination with the Pharmaceutical Composition I of the current invention may, for example, be selected from the existing drugs comprise typically of instillation of a prostaglandin, pilocarpine, epinephrine, or topical beta-blocker treatment, e.g. with timolol, as well as systemically administered inhibitors of carbonic anhydrase, e.g. acetazolamide. Cholinesterase inhibitors such as physostigmine and echothiopate may also be employed and have an effect similar to that of pilocarpine. Drugs currently used to treat glaucoma thus include, e.g., 1. Prostaglandin analogs such as latanoprost (Xalatan), bimatoprost (Lumigan) and travoprost (Travatan), which increase uveoscleral outflow of aqueous humor. Bimatoprost also increases trabecular outflow.
2. Topical beta-adrenergic receptor antagonists such as timolol, levobunolol (Betagan), and betaxolol, which decrease aqueous humor production by the ciliary body.
3. Alpha$_2$-adrenergic agonists such as brimonidine (Alphagan), which work by a dual mechanism, decreasing aqueous production and increasing uveo-scleral outflow.
4. Less-selective sympathomimetics like epinephrine and dipivefrin (Propine) increase outflow of aqueous humor through trabecular meshwork and possibly through uveoscleral outflow pathway, probably by a beta$_2$-agonist action.
5. Miotic agents (parasympathomimetics) like pilocarpine work by contraction of the ciliary muscle, tightening the trabecular meshwork and allowing increased outflow of the aqueous humour.
6. Carbonic anhydrase inhibitors like dorzolamide (Trusopt), brinzolamide (Azopt), acetazolamide (Diamox) lower secretion of aqueous humor by inhibiting carbonic anhydrase in the ciliary body.
7. Physostigmine is also used to treat glaucoma and delayed gastric emptying.

For example, the invention provides pharmaceutical compositions comprising a PDE1 inhibitor and a PDE2 inhibitor of the invention and an agent selected from (i) the prostanoids, unoprostone, latanoprost, travoprost, or bimatoprost; (ii) an alpha adrenergic agonist such as brimonidine, apraclonidine, or dipivefrin and (iii) a muscarinic agonist, such as pilocarpine. For example, the invention provides ophthalmic formulations comprising a PDE1 inhibitor and a PDE2 inhibitor of the invention together with bimatoprost, abrimonidine, brimonidine, timolol, or combinations thereof, in free or ophthamalogically acceptable salt form, in combination or association with an ophthamologically acceptable diluent or carrier. In addition to selecting a combination, however, a person of ordinary skill in the art can select an appropriate selective receptor subtype agonist or antagonist. For example, for alpha adrenergic agonist, one can select an agonist selective for an alpha$_1$ adrenergic receptor, or an agonist selective for an alpha$_2$ adrenergic receptor such as brimonidine, for example. For a beta-adrenergic receptor antagonist, one can select an antagonist selective for either $\beta_1$, or $\beta_2$, or $\beta_3$, depending on the appropriate therapeutic application. One can also select a muscarinic receptor agonist selective for a particular receptor subtype such as $M_1$-$M_5$.

The PDE1 inhibitor and the PDE2 inhibitor may be administered in the form of an ophthalmic composition, which includes an ophthalmic solution, cream or ointment. The ophthalmic composition may additionally include an intraocular-pressure lowering agent.

In yet another example, the PDE1 inhibitor and the PDE2 inhibitor disclosed may be combined with a subthreshold amount of an intraocular pressure-lowering agent which may be a bimatoprost ophthalmic solution, a brimonidine tartrate ophthalmic solution, or brimonidine tartrate/timolol maleate ophthalmic solution.

In addition to the above-mentioned methods, it has also been surprisingly discovered that PDE1 inhibitors and PDE2 inhibitors are useful to treat psychosis, for example, any conditions characterized by psychotic symptoms such as hallucinations, paranoid or bizarre delusions, or disorganized speech and thinking, e.g., schizophrenia, schizoaffective disorder, schizophreniform disorder, psychotic disorder, delusional disorder, and mania, such as in acute manic episodes and bipolar disorder. Without intending to be bound by any theory, it is believed that typical and atypical antipsychotic drugs such as clozapine primarily have their antagonistic activity at the dopamine D2 receptor. PDE1 inhibitors and PDE2 inhibitors, however, primarily act to enhance signaling at the dopamine D1 receptor. By enhancing D1 receptor signaling, PDE1 inhibitors can increase NMDA receptor function in various brain regions, for example in nucleus accumbens neurons and in the prefrontal cortex. This enhancement of function may be seen for example in NMDA receptors containing the NR2B subunit, and may occur e.g., via activation of the Src and protein kinase A family of kinases.

Therefore, the invention provides a new method for the treatment of psychosis, e.g., schizophrenia, schizoaffective disorder, schizophreniform disorder, psychotic disorder, delusional disorder, and mania, such as in acute manic episodes and bipolar disorder, comprising administering a therapeutically effective amount of the Pharmaceutical Composition I of the invention (e.g., comprising a phosphodiesterase-1 (PDE1) and PDE2 inhibitor combination of the invention, in free or pharmaceutically acceptable salt form) to a patient in need thereof.

PDE1 and PDE2 inhibitor combinations may be used in the foregoing methods of treatment or prophylaxis as the only therapeutic agents, but may also be used in combination or for co-administration with other active agents. Thus, the invention further comprises a method of treating psychosis, e.g., schizophrenia, schizoaffective disorder, schizophreniform disorder, psychotic disorder, delusional disorder, or mania, comprising administering, e.g., simultaneously, sequentially, or contemporaneously administering, therapeutically effective amounts of:

(i) the Pharmaceutical Composition I of the invention (e.g., comprising a PDE1 and PDE2 Inhibitor combination of the invention, in free or pharmaceutically acceptable salt form); and (ii) an antipsychotic, e.g., Typical antipsychotics, e.g., Butyrophenones, e.g. Haloperidol (Haldol, Serenace), Droperidol (Droleptan);

Phenothiazines, e.g., Chlorpromazine (Thorazine, Largactil), Fluphenazine (Prolixin), Perphenazine (Trilafon), Prochlorperazine (Compazine), Thioridazine (Mellaril, Melleril), Trifluoperazine (Stelazine), Mesoridazine, Periciazine, Promazine, Triflupromazine (Vesprin), Levomepromazine (Nozinan), Promethazine (Phenergan), Pimozide (Orap);

Thioxanthenes, e.g., Chlorprothixene, Flupenthixol (Depixol, Fluanxol), Thiothixene (Navane), Zuclopenthixol (Clopixol, Acuphase);

Atypical antipsychotics, e.g.,
Clozapine (Clozaril), Olanzapine (Zyprexa), Risperidone (Risperdal), Quetiapine (Seroquel), Ziprasidone (Geodon), Amisulpride (Solian), Paliperidone (Invega), Aripiprazole (Abilify), Bifeprunox; norclozapine,
in free or pharmaceutically acceptable salt form,
to a patient in need thereof.

The product or pharmaceutical composition of the invention may be used as the only therapeutic agents, or may also be used in combination or for co-administration with other active agents. For example, as PDE1 and PDE2 inhibitors potentiate the activity of D1 agonists, such as dopamine, they may be simultaneously, sequentially, or contemporaneously administered with conventional dopaminergic medications, such as levodopa and levodopa adjuncts (carbidopa, COMT inhibitors, MAO-B inhibitors), dopamine receptor agonists, and anticholinergics, e.g., in the treatment of a patient having Parkinson's disease. In addition, the PDE1 inhibitors and PDE2 inhibitors, e.g., as described herein, may also be administered in combination with estrogen/estradiol/estriol and/or progesterone/progestins to enhance the effectiveness of hormone replacement therapy or treatment of estrogen-induced endometrial hyperplasia or carcinoma.

The products and pharmaceutical compositions of the invention are particularly useful for the treatment of Parkinson's disease, schizophrenia, narcolepsy, glaucoma, female sexual dysfunction, cognitive disorder (e.g., learning, memory, recognition memory, social interactions and working memory), anxiety and depression.

In a particular embodiment, the products and pharmaceutical compositions of the invention are particularly useful for the treatment or prophylaxis of schizophrenia.

In still another aspect, the invention provides a method of lengthening or enhancing growth of the eyelashes by administering an effective amount of a prostaglandin analogue, e.g., bimatoprost, concomitantly, simultaneously or sequentially with an effective amount of the product or Pharmaceutical Composition I of the invention, to the eye of a patient in need thereof.

In yet another aspect, the invention provides a method for the treatment or prophylaxis of traumatic brain injury comprising administering a therapeutically effective amount of the Pharmaceutical Composition I of the invention to a patient in need thereof. Traumatic brain injury (TBI) encompasses primary injury as well as secondary injury, including both focal and diffuse brain injuries. Secondary injuries are multiple, parallel, interacting and interdependent cascades of biological reactions arising from discrete subcellular processes (e.g., toxicity due to reactive oxygen species, overstimulation of glutamate receptors, excessive influx of calcium and inflammatory upregulation) which are caused or exacerbated by the inflammatory response and progress after the initial (primary) injury. Abnormal calcium homeostasis is believed to be a critical component of the progression of secondary injury in both grey and white matter.

The present invention also provides
(i) the product or Pharmaceutical Composition I of the invention as hereinbefore described, for use in any of the methods or in the treatment of any disease or condition as hereinbefore set forth,
(ii) the use of the product or Pharmaceutical Composition I of the invention as hereinbefore described (in the manufacture of a medicament) for the treatment of any disease or condition as hereinbefore set forth,
(iii) the Pharmaceutical Composition I of the invention as hereinbefore described for use in the treatment of any disease or condition as hereinbefore set forth.

The invention also provides methods of treatment of any one or more of the following conditions:
(i) Neurodegenerative diseases, including Parkinson's disease, restless leg tremors, dyskinesias, Huntington's disease, Alzheimer's disease, and drug-induced movement disorders;
(ii) Mental disorders, including depression, attention deficit disorder, attention deficit hyperactivity disorder, bipolar illness, anxiety, sleep disorders, e.g., narcolepsy, cognitive impairment, dementia, Tourette's syndrome, autism, fragile X syndrome, psychostimulant withdrawal, and drug addiction;
(iii) Circulatory and cardiovascular disorders, including cerebrovascular disease, stroke, congestive heart disease, hypertension, pulmonary hypertension, pulmonary arterial hypertension, and sexual dysfunction;
(iv) Respiratory and inflammatory disorders, including asthma, chronic obstructive pulmonary disease, and allergic rhinitis, as well as autoimmune and inflammatory diseases;
(v) Any disease or condition characterized by low levels of cAMP and/or cGMP (or inhibition of cAMP and/or cGMP signaling pathways) in cells expressing PDE1 or PDE2; and/or
(vi) Any disease or condition characterized by reduced dopamine D1 receptor signaling activity,
comprising administering, e.g., simultaneously, sequentially, or contemporaneously administering, to a human or animal patient in need thereof an effective amount of (a) a PDE1 inhibitor, in free or pharmaceutically acceptable salt form, and (b) a PDE2 inhibitor, in free or pharmaceutically acceptable salt form. In some embodiments, the PDE1 inhibitor and PDE2 inhibitor are in a single dosage form. In other embodiments, the PDE1 inhibitor and PDE2 inhibitor are in separate dosage forms.

In one embodiment, the invention provides methods of treatment or prophylaxis for narcolepsy. In this embodiment, the PDE1 and PDE2 inhibitors, in free or pharmaceutically acceptable salt form, may be used as the only therapeutic agents, but may also be used in combination or for co-administration with other active agents. Thus, the invention further comprises a method of treating narcolepsy comprising administering, e.g., administering simultaneously, sequentially, or contemporaneously, therapeutically effective amounts of
(i) a PDE1 inhibitor, in free or pharmaceutically acceptable salt form,
(ii) a PDE2 inhibitor, in free or pharmaceutically acceptable salt form, and
(iii) optionally a compound to promote wakefulness or regulate sleep, e.g., selected from (a) central nervous system stimulants-amphetamines and amphetamine like compounds, e.g., methylphenidate, dextroamphetamine, methamphetamine, and pemoline; (b) modafinil, (c) antidepressants, e.g., tricyclics (including imipramine, desipramine, clomipramine, and protriptyline) and selective serotonin reuptake inhibitors (including fluoxetine and sertraline); and/or (d) gamma hydroxybutyrate (GHB), in free or pharmaceutically acceptable salt form,
to a human or animal patient in need thereof. The PDE1 and PDE2 inhibitors may be used as the only therapeutic agents or use in combination for co-administration with another active agent.

In another embodiment, the invention further provides methods of treatment or prophylaxis of a condition which may be alleviated by the enhancement of progesterone signaling comprising administering an effective amount of (a) a PDE1 inhibitor, in free or pharmaceutically acceptable salt form, and (b) a PDE2 inhibitor, in free or pharmaceutically acceptable salt form, to a human or animal patient in need thereof. Diseases or conditions that may be ameliorated by enhancement of progesterone signaling include, but are not limited to, female sexual dysfunction, secondary amenorrhea (e.g., exercise amenorrhoea), anovulation, menopause, menopausal symptoms, pre-menstrual syndrome, premature labor, infertility, for example infertility due to repeated miscarriage, irregular menstrual cycles, abnormal uterine bleeding, osteoporosis, autoimmmune disease, multiple sclerosis, prostate enlargement, prostate cancer, and hypothyroidism.

PDE1 and PDE2 inhibitors may be used in the foregoing methods of treatment or prophylaxis as the only therapeutic agents, but may also be used in combination or for co-administration with other active agents, for example in conjunction with hormone replacement therapy. Thus, the invention further comprises a method of treating disorders that may be ameliorated by enhancement of progesterone signaling comprising administering, e.g., administering simultaneously, sequentially, or contemporaneously, therapeutically effective amounts of (i) a PDE1 inhibitor, in free or pharmaceutically acceptable salt form,
(ii) a PDE2 inhibitor, in free or pharmaceutically acceptable salt form, and
(iii) a hormone, e.g., selected from estrogen and estrogen analogues (e.g., estradiol, estradiol esters) and progesterone and progesterone analogues (e.g., progestins), in free or pharmaceutically acceptable salt form, to a human or animal patient in need thereof.

The invention also provides a method for treating a PDE1 and/or PDE2-related disorder, a dopamine D1 receptor intracellular signaling pathway disorder, or disorders that may be alleviated by the enhancement of the progesterone signaling pathway in a patient in need thereof comprising administering, e.g., administering simultaneously, sequentially, or contemporaneously, to the patient an effective amount of (a) a PDE1 inhibitor, in free or pharmaceutically acceptable salt form, and (b) a PDE2 inhibitor, in free or pharmaceutically acceptable salt form, wherein PDE1 and PDE2 activity modulates phosphorylation of DARPP-32 and/or the GluR1 AMPA receptor.

In another aspect, the invention also provides a method for the treatment for glaucoma or elevated intraocular pressure comprising topical administration of a therapeutically effective amount of (a) a PDE1 inhibitor, in free or pharmaceutically acceptable salt form, and (b) a PDE2 inhibitor, in free or pharmaceutically acceptable salt form, in an ophthalmically compatible carrier to the eye of a patient in need thereof. However, treatment may also include a systemic therapy. Systemic therapy includes treatment that can directly reach the bloodstream, or oral methods of administration, for example.

Optionally, the PDE1 inhibitor and the PDE2 inhibitor may be administered sequentially or simultaneously with a third drug useful for treatment of glaucoma or elevated intraocular pressure. Where the PDE1 inhibitor and the PDE2 inhibitor are administered with other agents, the therapeutically effective amount of the third or subsequent agent may be below the amount needed for activity as monotherapy. Accordingly, a subthreshold amount (i.e., an amount below the level necessary for efficacy as monotherapy) may be considered therapeutically effective and also may also be referred alternatively as an effective amount. Indeed, an advantage of administering different agents with different mechanisms of action and different side effect profiles may be to reduce the dosage and side effects of either or both agents, as well as to enhance or potentiate their activity as monotherapy.

The optional additional agent or agents for use in combination with the PDE1 and PDE2 inhibitors of the current invention may, for example, be selected from the existing drugs comprise typically of instillation of a prostaglandin, pilocarpine, epinephrine, or topical beta-blocker treatment, e.g. with timolol, as well as systemically administered inhibitors of carbonic anhydrase, e.g. acetazolamide. Cholinesterase inhibitors such as physostigmine and echothiopate may also be employed and have an effect similar to that of pilocarpine. Drugs currently used to treat glaucoma thus include, e.g., 1. Prostaglandin analogs such as latanoprost (Xalatan), bimatoprost (Lumigan) and travoprost (Travatan), which increase uveoscleral outflow of aqueous humor. Bimatoprost also increases trabecular outflow.
2. Topical beta-adrenergic receptor antagonists such as timolol, levobunolol (Betagan), and betaxolol, which decrease aqueous humor production by the ciliary body.
3. Alpha$_2$-adrenergic agonists such as brimonidine (Alphagan), which work by a dual mechanism, decreasing aqueous production and increasing uveo-scleral outflow.
4. Less-selective sympathomimetics like epinephrine and dipivefrin (Propine) increase outflow of aqueous humor through trabecular meshwork and possibly through uveoscleral outflow pathway, probably by a beta$_2$-agonist action.
5. Miotic agents (parasympathomimetics) like pilocarpine work by contraction of the ciliary muscle, tightening the trabecular meshwork and allowing increased outflow of the aqueous humour.
6. Carbonic anhydrase inhibitors like dorzolamide (Trusopt), brinzolamide (Azopt), acetazolamide (Diamox) lower secretion of aqueous humor by inhibiting carbonic anhydrase in the ciliary body.
7. Physostigmine is also used to treat glaucoma and delayed gastric emptying.

The invention also provides a new method for the treatment of psychosis, e.g., schizophrenia, schizoaffective disorder, schizophreniform disorder, psychotic disorder, delusional disorder, and mania, such as in acute manic episodes and bipolar disorder, comprising administering, e.g., administering simultaneously, sequentially, or contemporaneously, a therapeutically effective amount of (a) a PDE1 inhibitor, in free or pharmaceutically acceptable salt form, and (b) a PDE2 inhibitor, in free or pharmaceutically acceptable salt form, to a patient in need thereof.

The PDE1 and PDE2 inhibitors may be used in the foregoing methods of treatment prophylaxis as the only therapeutic agents, but may also be used in combination or for co-administration with other active agents. Thus, the invention further comprises a method of treating psychosis, e.g., schizophrenia, schizoaffective disorder, schizophreniform disorder, psychotic disorder, delusional disorder, or mania, comprising administering, e.g., administering simultaneously, sequentially, or contemporaneously, therapeutically effective amounts of:

(i) a PDE1 inhibitor, in free or pharmaceutically acceptable salt form,
(ii) a PDE2 inhibitor, in free or pharmaceutically acceptable salt form, and
(iii) optionally an antipsychotic, e.g.,
Typical antipsychotics, e.g.,
Butyrophenones, e.g. Haloperidol (Haldol, Serenace), Droperidol (Droleptan);
Phenothiazines, e.g., Chlorpromazine (Thorazine, Largactil), Fluphenazine (Prolixin), Perphenazine (Trilafon), Prochlorperazine (Compazine), Thioridazine (Mellaril, Melleril), Trifluoperazine (Stelazine), Mesoridazine, Periciazine, Promazine, Triflupromazine (Vesprin), Levomepromazine (Nozinan), Promethazine (Phenergan), Pimozide (Orap);
Thioxanthenes, e.g., Chlorprothixene, Flupenthixol (Depixol, Fluanxol), Thiothixene (Navane), Zuclopenthixol (Clopixol, Acuphase);
Atypical antipsychotics, e.g.,
Clozapine (Clozaril), Olanzapine (Zyprexa), Risperidone (Risperdal), Quetiapine (Seroquel), Ziprasidone (Geodon), Amisulpride (Solian), Paliperidone (Invega), Aripiprazole (Abilify), Bifeprunox; norclozapine,
in free or pharmaceutically acceptable salt form,
to a patient in need thereof.

In still another aspect, the invention provides a method of lengthening or enhancing growth of the eyelashes by administering an effective amount of a prostaglandin analogue, e.g., bimatoprost, concomitantly, simultaneously or sequentially with an effective amount of (a) a PDE1 inhibitor, in free or pharmaceutically acceptable salt form, and (b) a PDE2 inhibitor, in free or pharmaceutically acceptable salt form, to the eye of a patient in need thereof.

In yet another aspect, the invention provides a method for the treatment or prophylaxis of traumatic brain injury comprising administering a therapeutically effective amount of (a) a PDE1 inhibitor, in free or pharmaceutically acceptable salt form, and (b) a PDE2 inhibitor, in free or pharmaceutically acceptable salt form, to a patient in need thereof. Traumatic brain injury (TBI) encompasses primary injury as well as secondary injury, including both focal and diffuse brain injuries. Secondary injuries are multiple, parallel, interacting and interdependent cascades of biological reactions arising from discrete subcellular processes (e.g., toxicity due to reactive oxygen species, overstimulation of glutamate receptors, excessive influx of calcium and inflammatory upregulation) which are caused or exacerbated by the inflammatory response and progress after the initial (primary) injury. Abnormal calcium homeostasis is believed to be a critical component of the progression of secondary injury in both grey and white matter.

The present invention also provides
(i) use of (a) a PDE1 inhibitor, in free or pharmaceutically acceptable salt form, and (b) a PDE2 inhibitor, in free or pharmaceutically acceptable salt form, e.g., in single or separate dosage forms, in any of the methods or in the treatment of any disease or condition as hereinbefore set forth,
(ii) the use of (a) a PDE1 inhibitor, in free or pharmaceutically acceptable salt form, and (b) a PDE2 inhibitor, in free or pharmaceutically acceptable salt form (in the manufacture of a medicament) for the treatment of any disease or condition as hereinbefore set forth.

The present invention also provides a kit comprising (a) a PDE1 inhibitor, in free or pharmaceutically acceptable salt form, and (b) a PDE2 inhibitor, in free or pharmaceutically acceptable salt form.

The present invention also provides
(i) use of a kit comprising (a) a PDE1 inhibitor, in free or pharmaceutically acceptable salt form, and (b) a PDE2 inhibitor, in free or pharmaceutically acceptable salt form, e.g., in single or separate dosage forms, in any of the methods or in the treatment of any disease or condition as hereinbefore set forth,
(ii) the use of a kit comprising (a) a PDE1 inhibitor, in free or pharmaceutically acceptable salt form, and (b) a PDE2 inhibitor, in free or pharmaceutically acceptable salt form, for the treatment of any disease or condition as hereinbefore set forth.

BRIEF DESCRIPTION OF THE DRAWINGS

FIG. 1 is a graph which illustrates the results of the Enzyme Immunoassay described in Example 6.

DETAILED DESCRIPTION OF THE INVENTION

PDE1 and PDE2 inhibitors are known in the art. In a particular embodiment of the invention, a PDE1 inhibitor of the current invention includes those disclosed in WO 2006/133261, WO 2007/143705, WO 2008/063505, WO 2008/070095, WO 2009/075784, WO 2009/073210, WO 2010/065153, WO 2010/065148, WO 2010/065151, WO 2010/065149, WO 2010/065147, WO 2010/065152, WO 2010/098839, WO 2010/132127, WO 2011/153129, WO 2011/153135, WO 2011/153136, WO 2011/153138, WO 2012/171016, the contents of each of which are incorporated by reference in their entirety. In another particular embodiment, the PDE1 inhibitor is (6aR,9aS)-5,6a,7,8,9,9a-hexahydro-5-methyl-3-(phenylamino)-2-((4-Pyridin-2yl)-benzyl)-cyclopent[4,5]imidazo[1,2-a]pyrazolo[4,3-e]pyrimidin-4(2H)-one, in free or salt form. In another particular embodiment, the PDE1 inhibitor is (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one, in free or salt form.

In another particular embodiment, a PDE2 inhibitor of the current invention includes those disclosed in WO 2010/054260, WO 2010/054253, WO 2012/104293, WO 2013/000924, WO 2013/034755, WO 2013/034758, WO 2013/034761, WO 2006/072615, WO 2006/024640, WO 2006/072612, WO 2012/114222, WO 2012/168817, WO 2005/041957, WO 2005/061497, WO 2011/011312, EP 1749824, EP 1548011, EP 1556055, U.S. Pat. No. 4,766,122, WO 2002/068423, WO 2002/050078, WO 2002/009713, WO 98/32755, U.S. Pat. No. 5,861,396, WO 2004/089953, U.S. Pat. No. 5,861,396 and U.S. Pat. No. 6,573,263. In a particular embodiment, the PDE2 inhibitor of the invention is 2-(3,4-Dimethoxybenzyl)-7-{(1R)-1-[(1R)-1-hydroxyethyl]-4-phenylbutyl}-5-methylimidazo[5,1-f][1,2,4]triazin-4(3H)-one (BAY 60-7550), in free or salt form.

In this specification, unless otherwise indicated, the PDE1 and PDE2 inhibitors of the invention are to be understood as embracing the compounds in any form, for example free or acid addition salt form, or where the compounds contain acidic substituents, in base addition salt form. The PDE1 and PDE2 inhibitors are intended for use as pharmaceuticals, therefore pharmaceutically acceptable salts are preferred. Salts which are unsuitable for pharmaceutical uses may be useful, for example, for the isolation or purification of the free compounds or their pharmaceutically acceptable salts, and are therefore also included.

The PDE1 inhibitor and PDE2 inhibitor of the invention may in some cases also exist in prodrug form. A prodrug form of PDE1 or PDE2 inhibitor may be inactive or less active outside the body and converts in the body to an active PDE1 or PDE2 inhibitory compound, respectively. For example when the PDE1 or PDE2 inhibitor of the invention contains a hydroxy or carboxy substituent, this substituent may form physiologically hydrolysable and acceptable esters. As used herein, "physiologically hydrolysable and acceptable ester" means esters of the PDE1 or PDE2 inhibitor of the invention which are hydrolysable under physiological conditions to yield acids (in the case of PDE1 or PDE2 inhibitor of the invention which have hydroxy substituents) or alcohols (in the case of PDE1 or PDE2 inhibitor of the invention which have carboxy substituents) which are themselves physiologically tolerable at doses to be administered. Therefore, wherein the PDE1 or PDE2 inhibitor of the invention contains a hydroxy group, for example, compound-OH, the acyl ester prodrug of such compound, for example, compound-O—C(O)—$C_{1-4}$alkyl, can hydrolyze in the body to form physiologically hydrolysable alcohol (compound-OH) on the one hand and acid on the other (e.g., HOC(O)—$C_{1-4}$alkyl). Alternatively, wherein the compound of the invention contains a carboxylic acid, for example, compound-C(O)OH, the acid ester prodrug of such compound, for example, compound-C(O)O—$C_{1-4}$alkyl can hydrolyze to form compound-C(O)OH and HO—$C_{1-4}$alkyl. As will be appreciated the term thus embraces conventional pharmaceutical prodrug forms.

The PDE1 and PDE2 inhibitors of the invention include their enantiomers, diastereoisomers and racemates, as well as their polymorphs, hydrates, solvates and complexes. Some individual compounds within the scope of this invention may contain double bonds. Representations of double bonds in this invention are meant to include both the E and the Z isomer of the double bond. In addition, some compounds within the scope of this invention may contain one or more asymmetric centers. This invention includes the use of any of the optically pure stereoisomers as well as any combination of stereoisomers.

As will be appreciated by those skilled in the art, the PDE1 and PDE2 inhibitors of the invention may exhibit keto-enol tautomerization. Therefore, the invention as defined in the present invention is to be understood as embracing both the structures as set forth herewith and their tautomeric forms.

It is also intended that the PDE1 and PDE2 inhibitors of the invention encompass their stable and unstable isotopes. Stable isotopes are nonradioactive isotopes which contain one additional neutron compared to the abundant nuclides of the same species (i.e., element). It is expected that the activity of compounds comprising such isotopes would be retained, and such compound would also have utility for measuring pharmacokinetics of the non-isotopic analogs. For example, the hydrogen atom at a certain position on the Compounds of the Invention may be replaced with deuterium (a stable isotope which is non-radioactive). Examples of known stable isotopes include, but not limited to, deuterium, $^{13}C$, $^{15}N$, $^{18}O$. Alternatively, unstable isotopes, which are radioactive isotopes which contain additional neutrons compared to the abundant nuclides of the same species (i.e., element), e.g., $^{123}I$, $^{131}I$, $^{125}I$, $^{11}C$, $^{18}F$, may replace the corresponding abundant species, e.g., I, C and F respectively. Another example of useful isotope of the compound of the invention is the $^{11}C$ isotope. These radio isotopes are useful for radio-imaging and/or pharmacokinetic studies of the compounds of the invention. Methods of making isotopes of PDE1 inhibitors disclosed in WO 2011/043816, the contents of which are incorporated by reference in their entirety, may be used for making the isotopes of the compounds of the current invention.

The phrase "PDE1 inhibitor(s) of the invention" encompasses any and all of the compounds disclosed herewith, in free or (pharmaceutically) salt form. Preferably, the PDE1 inhibitors of the invention inhibit phosphodiesterase-mediated (e.g., PDE1-mediated) hydrolysis of cGMP, e.g., with an $IC_{50}$ of less than 100 nM in an immobilized-metal affinity particle reagent PDE assay, for example, as described in Example 3. Preferably, the PDE1 inhibitors of the invention are (6aR,9aS)-5,6a,7,8,9,9a-hexahydro-5-methyl-3-(phenylamino)-2-((4-Pyridin-2yl)-benzyl)-cyclopent[4,5]imidazo[1,2-a]pyrazolo[4,3-e]pyrimidin-4(2H)-one or (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one, in free or salt form.

The phrase "PDE2 inhibitor(s) of the invention" encompasses any and all of the compounds disclosed herewith, in free or (pharmaceutically) salt form. Preferably, the PDE2 inhibitors of the invention inhibit phosphodiesterase-mediated (e.g., PDE2-mediated) hydrolysis of cGMP, e.g., with an $IC_{50}$ of less than 100 nM in an immobilized-metal affinity particle reagent PDE assay, for example, as described in Example 5. Preferably, the PDE2 inhibitor of the invention is 2-(3,4-Dimethoxybenzyl)-7-{(1R)-1-[(1R)-1-hydroxyethyl]-4-phenylbutyl}-5-methylimidazo[5,1-f][1,2,4]triazin-4(3H)-one (BAY 60-7550), in free or salt form.

The words "treatment" and "treating" are to be understood accordingly as embracing prophylaxis and treatment or amelioration of symptoms of disease as well as treatment of the cause of the disease.

For methods of treatment, the word "effective amount" is intended to encompass a therapeutically effective amount to treat a specific disease or disorder.

The term "patient" include human or non-human (i.e., animal) patient. In particular embodiment, the invention encompasses both human and nonhuman. In another embodiment, the invention encompasses nonhuman. In other embodiment, the term encompasses human.

The term "comprising" as used in this disclosure is intended to be open-ended and does not exclude additional, unrecited elements or method steps.

The product and pharmaceutical composition of the invention are in particular useful for the treatment of Parkinson's disease, schizophrenia, narcolepsy, glaucoma, female sexual dysfunction, cognitive disorder (e.g., learning, memory, recognition memory, social interactions and working memory), anxiety and depression.

Dosages employed in practicing the present invention will of course vary depending, e.g. on the particular disease or condition to be treated, the particular PDE1 inhibitor and PDE2 inhibitor used, the mode of administration, and the therapy desired. The PDE1 inhibitor and PDE2 inhibitor may be administered by any suitable route, including orally, parenterally, transdermally, or by inhalation, but are preferably administered orally. In general, satisfactory results, e.g. for the treatment of diseases as hereinbefore set forth are indicated to be obtained on oral administration at dosages of the order from about 0.01 to 3.0 mg/kg. In larger mammals, for example humans, an indicated daily dosage for oral administration will accordingly be in the range of from about 0.75 to 150 mg, conveniently administered once, or in divided doses 2 to 4 times, daily or in sustained release form. Unit dosage forms for oral administration thus for example may comprise from about 0.2 to 75 or 150 mg, e.g. from about 0.2 or 1.0 or 2.0 to 50, 75 or 100 mg of the PDE1 or PDE2 inhibitor, together with a pharmaceutically acceptable diluent or carrier therefore. The PDE1 inhibitor(s) and PDE2 inhibitor(s) may be in a single dosage form or separate dosage forms. The PDE1 inhibitor(s) and PDE2 inhibitor(s) may be administered in the same or different amounts.

Pharmaceutical compositions comprising Compounds of the Invention may be prepared using conventional diluents or excipients and techniques known in the galenic art. Thus oral dosage forms may include tablets, capsules, solutions, suspensions and the like.

EXAMPLES

The PDE1 inhibitors of the invention and their pharmaceutically acceptable salts may be made using the methods as described and exemplified or similarly described or similarly exemplified in WO 2006/133261, WO 2007/143705, WO 2008/063505, WO 2008/070095, WO 2009/075784, WO 2009/073210, WO 2010/065153, WO 2010/065148, WO 2010/065151, WO 2010/065149, WO 2010/065147, WO 2010/065152, WO 2010/098839, WO 2010/132127, WO 2011/153129, WO 2011/153135, WO 2011/153136, WO 2011/153138, WO 2012/171016, the contents of each of which are incorporated by reference in their entirety. The PDE2 inhibitors of the invention may be made using the methods as described and exemplified or similarly described or similarly exemplified in WO 2010/054260, WO 2010/054253, WO 2012/104293, WO 2013/000924, WO 2013/034755, WO 2013/034758, WO 2013/034761, WO 2006/072615, WO 2006/024640, WO 2006/072612, WO 2012/114222, WO 2012/168817, WO 2005/041957, WO 2005/061497, WO 2011/011312, EP 1749824, EP 1548011, EP 1556055, U.S. Pat. No. 4,766,122, WO 2002/068423, WO 2002/050078, WO 2002/009713, WO 98/32755, U.S. Pat. No. 5,861,396, WO 2004/089953, U.S. Pat. No. 5,861,396, and U.S. Pat. No. 6,573,263, the contents of each of which are incorporated by reference in their entirety. If not commercially available, starting materials for these processes may be made by procedures, which are selected from the chemical art using techniques which are similar or analogous to the synthesis of known compounds.

In particular, the synthetic methods for (6aR,9aS)-5,6a,7,8,9,9a-hexahydro-5-methyl-3-(phenylamino)-2-((4-Pyridin-2yl)-benzyl)-cyclopent[4,5]imidazo[1,2-a]pyrazolo[4,3-e]pyrimidin-4(2H)-one and (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one, in free or salt form, may be prepared using the procedure set forth or similarly set forth below in Examples 1 and 2.

Example 1—(6aR,9aS)-5,6a,7,8,9,9a-hexahydro-5-methyl-3-(phenylamino)-2-((4-Pyridin-2yl)-benzyl)-cyclopent[4,5]imidazo[1,2-a]pyrazolo[4,3-e]pyrimidin-4(2H)-one This compound may be prepared as described or similarly described in WO 2006/133261. Step (a) 7-(4-Methoxybenzyl)-5-methyl-3-(phenylamino)-1H-pyrazolo[3,4-d]pyrimidine-4,6(5H,7H)-dione: Phenyl isothiocyanate (3.9 mL, 32.7 mmol) is added to a suspension of 6-hydrazinyl-1-(4-methoxybenzyl)-3-methylpyrimidine-2,4(1H,3H)-dione (0.45 g, 1.6 mmol) in DMF (12 mL). The reaction mixture is heated at 120° C. for 40 hours, and then evaporated to remove solvent under reduced pressure. The residue is washed with hexanes, and then treated with MeOH (125 mL), and stored at −15° C. for 2 days to give a crystalline solid. The solid is recrystallized from $CH_3OH$-EtOAc to afford 2.5 g product.

Step (b) 5-Methyl-3-(phenylamino)-1H-pyrazolo[3,4-d]pyrimidine-4,6(5H,7H)-dione: $AlCl_3$ (0.733 g, 5.50 mmol) is added to a solution of 7-(4-methoxybenzyl)-5-methyl-3-(phenylamino)-1H-pyrazolo[3,4-d]pyrimidine-4,6(5H,7H)-dione (0.692 g, 1.83 mmol) and anisole (40 μL, 0.367 mmol) in 1,2-dichloroethane (10 mL) under argon. The reaction mixture is stirred at room temperature for 30 min, and then quenched with water with cooling. The resulting suspension is filtered through a layer of celite and the celite is washed with MeOH (20 mL). The product is eluted from the celite with a large amount of THF. The THF eluent is evaporated to afford 0.47 g of product.

Step (c) 6-Chloro-5-methyl-3-(phenylamino)-1H-pyrazolo[3,4-d]pyrimidin-4(5H)-one: 5-methyl-3-(phenylamino)-1H-pyrazolo[3,4-d]pyrimidine-4,6(5H,7H)-dione (450 mg, 1.75 mmol) is refluxed in $POCl_3$ (20 mL) for 60 hours, and the mixture is evaporated to dryness. The residue is purified by silica gel flash chromatography to give 122 mg product as white solids and 207 mg starting material is recovered.

Step (d) 6-((1R,2R)-2-hydroxycyclopentylamino)-5-methyl-3-(phenylamino)-1H-pyrazolo[3,4-d]pyrimidin-4(5H)-one: A solution of 6-chloro-5-methyl-3-(phenylamino)-1H-pyrazolo[3,4-d]pyrimidin-4(5H)-one (75.8 mg, 0.275 mmol), (1R,2R)-2-amino-cyclopentanol (0.55 mmol) and DIPEA (144 μL, 0.825 mmol) in DMF (3 mL) is heated at 110° C. overnight. The reaction mixture is evaporated to remove DMF under reduced pressure. The residue is then purified by chromatography to give the desired product.

Step (e) (6aR,9aS)-5,6a,7,8,9,9a-hexahydro-5-methyl-3-(phenylamino)-cyclopent[4,5]imidazo[1,2-a]pyrazolo[4,3-e]pyrimidin-4(2H)-one: 2.0 M solution of thionyl chloride in $CH_2Cl_2$ (267 μL, 0.534 mmol) is added to a solution of 6-((1R,2R)-2-hydroxycyclopentylamino)-5-methyl-3-(phenylamino)-1H-pyrazolo[3,4-d]pyrimidin-4(5H)-one (30 mg, 0.088 mmol) in $CH_2Cl_2$ (1 mL) and THF (1.5 mL). The reaction mixture is stirred at r.t. overnight, and then quenched with 29 μL of 28% $NH_4OH$. The resulting mixture is concentrated and purified by chromatography to give 26 mg product as white solids.

Step (f) (6aR,9aS)-5,6a,7,8,9,9a-hexahydro-5-methyl-3-(phenylamino)-2-((4-Pyridin-2yl)-benzyl)-cyclopent[4,5]imidazo[1,2-a]pyrazolo[4,3-e]pyrimidin-4(2H)-one: A mixture of (6aR,9aS)-5,6a,7,8,9,9a-hexahydro-5-methyl-3-(phenylamino)-cyclopent[4,5]imidazo[1,2-a]pyrazolo[4,3-e]pyrimidin-4(2H)-one (22 mg, 0.068 mmol), 2-(4-(bromomethyl)phenyl)pyridine (16.9 mg, 0.068 mmol), and $K_2CO_3$ (9.4 mg, 0.068 mmol) in DMF (2.5 mL) is stirred at room temperature overnight under argon. The reaction mixture is purified by a semi-preparative HPLC to give the final product.

Example 2—(6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one

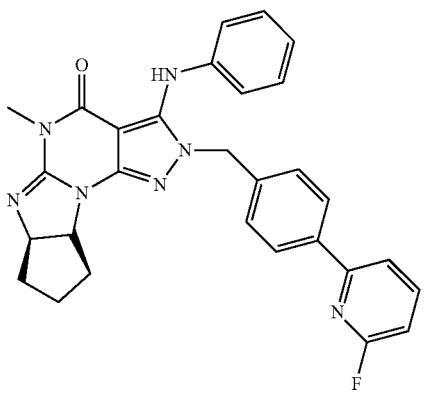

This compound may be prepared as described or similarly described in WO 2007/143705, WO 2013/192556, U.S. Prov. Appl. Nos. 61/838,105 and 61/919,424, the contents of which are incorporated by reference in their entirety.

Example 3—Measurement of PDE1 Inhibition In Vitro Using IMAP Phosphodiesterase Assay Kit Phosphodiesterase 1B (PDE1B) is a calcium/calmodulin dependent phosphodiesterase enzyme that converts cyclic guanosine monophosphate (cGMP) to 5'-guanosine monophosphate (5'-GMP). PDE1B can also convert a modified cGMP substrate, such as the fluorescent molecule cGMP-fluorescein, to the corresponding GMP-fluorescein. The generation of GMP-fluorescein from cGMP-fluorescein can be quantitated, using, for example, the IMAP (Molecular Devices, Sunnyvale, Calif.) immobilized-metal affinity particle reagent.

Briefly, the IMAP reagent binds with high affinity to the free 5'-phosphate that is found in GMP-fluorescein and not in cGMP-fluorescein. The resulting GMP-fluorescein—IMAP complex is large relative to cGMP-fluorescein. Small fluorophores that are bound up in a large, slowly tumbling, complex can be distinguished from unbound fluorophores, because the photons emitted as they fluoresce retain the same polarity as the photons used to excite the fluorescence.

In the phosphodiesterase assay, cGMP-fluorescein, which cannot be bound to IMAP, and therefore retains little fluorescence polarization, is converted to GMP-fluorescein, which, when bound to IMAP, yields a large increase in fluorescence polarization (Δmp). Inhibition of phosphodiesterase, therefore, is detected as a decrease in Δmp.

Enzyme Assay

Materials: All chemicals are available from Sigma-Aldrich (St. Louis, Mo.) except for IMAP reagents (reaction buffer, binding buffer, FL-GMP and IMAP beads), which are available from Molecular Devices (Sunnyvale, Calif.).

Assay: 3',5'-cyclic-nucleotide-specific bovine brain phosphodiesterase (Sigma, St. Louis, Mo.) is reconstituted with 50% glycerol to 2.5 U/ml. One unit of enzyme will hydrolyze 1.0 μmole of 3',5'-cAMP to 5'-AMP per min at pH 7.5 at 30° C. One part enzyme is added to 1999 parts reaction buffer (30 μM $CaCl_2$, 10 U/ml of calmodulin (Sigma P2277), 10 mM Tris-HCl pH 7.2, 10 mM $MgCl_2$, 0.1% BSA, 0.05% $NaN_3$) to yield a final concentration of 1.25 mU/ml. 99 μl of diluted enzyme solution is added into each well in a flat bottom 96-well polystyrene plate to which 1 μl of test compound dissolved in 100% DMSO is added. Selected Compounds of the Invention are mixed and pre-incubated with the enzyme for 10 min at room temperature.

The FL-GMP conversion reaction is initiated by combining 4 parts enzyme and inhibitor mix with 1 part substrate solution (0.225 μM) in a 384-well microtiter plate. The reaction is incubated in dark at room temperature for 15 min. The reaction is halted by addition of 60 μl of binding reagent (1:400 dilution of IMAP beads in binding buffer supplemented with 1:1800 dilution of antifoam) to each well of the 384-well plate. The plate is incubated at room temperature for 1 hour to allow IMAP binding to proceed to completion, and then placed in an Envision multimode microplate reader (PerkinElmer, Shelton, Conn.) to measure the fluorescence polarization (Δmp).

A decrease in GMP concentration, measured as decreased Δmp, is indicative of inhibition of PDE activity. $IC_{50}$ values are determined by measuring enzyme activity in the presence of 8 to 16 concentrations of compound ranging from 0.0037 nM to 80,000 nM and then plotting drug concentration versus ΔmP, which allows $IC_{50}$ values to be estimated using nonlinear regression software (XLFit; IDBS, Cambridge, Mass.).

The PDE1 inhibitors may be selected and tested in an assay as described or similarly described herein for PDE1 inhibitory activity. Using the procedure described or similarly described in this example, the compound of Example 1 has an $IC_{50}$ value of 105+/−10.9 pM.

Example 4—2-(3,4-Dimethoxybenzyl)-7-{(1R)-1-[(1R)-1-hydroxyethyl]-4-phenylbutyl}-5-methylimidazo[5,1-f][1,2,4]triazin-4(3H)-one (BAY 60-7550)

The compound of this example may be prepared as described or similarly described in U.S. Pat. No. 6,573,263, the contents of which are incorporated by reference in their entirety. The details are reproduced below:

Compound 4A: 2-(3,4-Dimethoxybenzyl)-7-[1-(1-hydroxyethyl)-4-phenylbutyl]-5-methylimidazo-[5,14][1,2,4]triazin-4(3H)-one 110 mg (0.22 mmol) of 7-(1-acetyl-4-phenylbutyl)-2-(3,4-dimethoxybenzyl)-5-methylimidazo[5,1-f][1,2,4]triazin-4(3H)-one are dissolved in 5 ml of ethanol and treated in portions with 20 mg (0.53 mmol) of sodium borohydride to give 2-(3,4-dimethoxybenzyl)-7-[1-(1-hydroxyethyl)-4-phenylbutyl]-5-methylimidazo[5,1-f][1,2,4]triazin-4(3H)-one.

Compound 4A is separated into the two diastereomeric compounds by chromatography under reversed phase conditions (Stability C30, 5 μm) using acetonitrile/water (1/1, v/v) as eluent. The corresponding enantiomerically pure compounds (Examples 4B, 4C, 4D and 4E below) can be obtained by chromatographic separation of the racemic diastereomers on a chiral stationary silica gel phase.

Particularly suitable chiral stationary polyamide silica gel phases (CSP) for the separation of the racemates are those based on the monomers N-methacryloyl-L-leucine-d-menthylamide or N-methacryloyl-L-leucine-1-menthylamide (cf. EP-A-0 379 917) using, for example, ethyl acetate as eluent.

The chromatographic resolution of the first-eluting diastereomers from Example 4A yields the two enantiomers Compound 4B 2-(3,4-Dimethoxybenzyl)-7-{(1R)-1-[(1R)-1-hydroxyethyl]-4-phenylbutyl}-5-methylimidazo[5,1-f][1,2,4]triazin-4(3H)-one (BAY 60-7550) and Compound 4C 2-(3,4-Dimethoxybenzyl)-7-{(1S)-1-[(1S)-1-hydroxyethyl]-4-phenylbutyl}-5-methyl-imidazo[5,1-f][1,2,4]triazin-4 (3H)-one. Analogously to this, the two enantiomers Compound 4D 2-(3,4-Dimethoxybenzyl)-7-{(1R)-1-[(1S)-1-hydroxyethyl]-4-phenylbutyl}-5-methylimidazo[5,1-f][1,2,4]triazin-4(3H)-one and Compound 4E 2-(3,4-Dimethoxybenzyl)-7-{(1S)-1-[(1R)-1-hydroxyethyl]4-phenylbutyl}-5-methylimidazo[5,1-f][1,2,4]triazin-4(3H)-one are obtained from the later-eluting diastereomers. The separation of the enantiomers Compound 4D and Compound 4E is carried out analogously to Compound 4B starting from the later eluting diastereomer.

Moreover, the Compound 4B and Compound 4C can also preferably be obtained by diastereoselective reduction of 7-(1-acetyl-4-phenylbutyl)-2-(3,4-dimethoxybenzyl)-5-methylimidazo[5,1-f][1,2,4]triazin-4(3H)-one. For this, 190 mg (0.41 mmol) of 7-(1-acetyl-4-phenylbutyl)-2-(3,4-dimethoxy-benzyl)-5-methylimidazo[5,1-f][1,2,4]triazin-4(3H)-one are dissolved in 20 ml of dichloromethane/methanol 100/1 and, treated with 6.10 mg (0.45 mmol) of zinc chloride, stirred at room temperature for 30 min. After cooling to 0° C., 30 mg of sodium borohydride are added in portions and the mixture is then stirred for 2.5 h with ice-bath cooling. The batch is then neutralized using a few drops of 2 N hydrochloric acid, concentrated in vacuo and chromatographed using the eluent dichloromethane/methanol 80/1 and 40/1. The diastereomer mixture is then purified under reversed phase chromatographic conditions as mentioned in Example 4B and separated into the pure enantiomers by chromatography on the chiral stationary phase.

Example 5—Measurement of PDE2 Inhibition In Vitro

Inhibition of PDE2 may be measured by using an assay similarly described in Example 3 except PDE2 enzyme (human recombinant) is used instead of PDE1 enzyme, fluorescent-cAMP is used as substrate, and cGMP (1 µM) is added to stimulate the enzyme.

Alternatively, PDE2 inhibition may be measured as described or similarly described in Boess et al., *Neuropharmacology*, Volume 47, Issue 7, December 2004, Pages 1081-1092, the contents of which are incorporated by reference in their entirety. Using the procedure described or similarly described in Boess et al., the exemplified Compound 4B (Bay-60-7550) is reported to have an $IC_{50}$ value of 2.0 nM (bovine) and 4.7 nM (human).

Example 6—Effect of PDE1 and PDE2 Inhibitor on Nitric Oxide Signaling in the Brain Animals:

All handling and use of animals follow a protocol approved by Institutional Animal Care and Use Committee (IACUC) of Columbia University, in accordance with NIH guidelines. Male, C57BL/6 mice (7-8 weeks of age) are obtained from Jackson Laboratory. Up to five mice are housed per cage and are maintained under 12-hour light/dark cycles with standard Purina rodent chow and water ad libitum.

Slice Preparation:

Slice preparation may be carried out as described below or similarly described in Nishi et al., *J. Neuroscience* (2008) 28:10460-71, the contents of which are incorporated by reference. Male C57BL/6 mice at 6-8 weeks old are purchased from Japan SLC. All mice used are handled in accordance with the Declaration of Helsinki and with the *Guide for the Care and Use of Laboratory Animals* as adopted and promulgated by the National Institutes of Health, and the specific protocols are approved by the Institutional Animal Care and Use Committee of Kurume University School of Medicine. Male C57BL/6 mice are killed by decapitation. The brains are rapidly removed and placed in ice-cold, oxygenated Krebs-$HCO_3^-$ buffer [(in mM) 124 NaCl, 4 KCl, 26 $NaHCO_3$, 1.5 $CaCl_2$, 1.25 $KH_2PO_4$, 1.5 MgSO4, and 10 D-glucose, pH 7.4]. Coronal slices (350 µm) are prepared using a vibrating blade microtome, VT1000S (Leica Microsystems), as described previously (Nishi et al., *PNAS* (2005) 102:1199-1204). *Striata* are dissected from the slices in ice-cold Krebs-$HCO_3^-$ buffer.

Slice Treatment:

Each slice is placed in a polypropylene incubation tube with 2 ml of fresh Krebs-$HCO_3^-$ buffer containing adenosine deaminase (10 µg/ml). The slices are pre-incubated at 30° C. under constant oxygenation with 95% O2/5% CO2 for 60 min. The buffer is replaced with fresh Krebs-$HCO_3^-$ buffer after 30 min of pre-incubation. Slices are treated for 45 minutes with a PDE1 inhibitor alone, PDE2 inhibitor alone, PDE1 inhibitor in combination with PDE2 inhibitor or a control (DMSO vehicle with no PDE1 or PDE2 inhibitor). The PDE1 inhibitor compound (6aR,9aS)-5,6a,7,8,9,9a-hexahydro-5-methyl-3-(phenylamino)-2-((4-Pyridin-2yl)-benzyl)-cyclopent[4,5]imidazo[1,2-a]pyrazolo[4,3-e]pyrimidin-4(2H)-one (Example 1) at 1 µM is used. PDE2 is blocked using 0.1 µM of 2-(3,4-Dimethoxybenzyl)-7-{(1R)-1-[(1R)-1-hydroxyethyl]-4-phenylbutyl}-5-methylimidazo [5,1-f][1,2,4]triazin-4(3H)-one (BAY 60-7550 or Example 4B). Following the pretreatment, the slices are stimulated with 5 µM of the NO donor, diethylammonium (Z)-1-(N,N-diethylamino)diazen-1-ium-1,2-diolate (DEA/NO) for 4 min, in Krebs as indicated, without adenosine deaminase. DEA/NO is used for its ability to elicit a dose-dependent change in cGMP levels. DEA/NO in a stock solution of 0.1N NaOH are prepared and diluted in Krebs buffer to either 0.5 µM or 5 µM immediately before application to each slice. Immediately following stimulation, the Krebs is removed and replaced with 5% trichloroacetic acid and sonicated. Samples are stored on ice before being centrifuged at 15,000×g for 20 minutes at 4° C. The supernatant is reserved for the cyclic nucleotide enzyme immunoassay and the precipitated protein pellet is re-suspended in 60 ul Laemmli sample buffer. Each is stored at −80° C. until use.

Enzyme Immunoassay:

The reserved supernatants are washed three times with 5× volume ethyl ether to remove the TCA. The samples are then dried under vacuum (Speedvac, Savant SPD111V) at room temperature. In preparation for either the cGMP or cAMP enzyme immunoassay (Cayman Chemical Co, Ann Arbor, Mich.), they are resuspended in 100 µL EIA buffer. The samples are acetylated and analyzed in comparison to provided standards according to kit instructions. The results from the colorometric assay are recorded by the SoftMax 4.8 software (Molecular Devices, Sunnyvale, Calif.). Each data point is converted to % $B/B_0$ (100*[(sample or standard OD–average non-specific binding)/(average $B_0$–average non-specific binding)]). The standards are plotted and fit to a 4-parameter logistic equation. The concentrations of the samples are interpolated from the standard curve using Microsoft Excel and GraphPad Prizm. The result of this experiment is illustrated in FIG. 1. This experiment shows that the combination of inhibition of PDE1 and PDE2 has a greater than additive effect on cGMP levels in the striatum under conditions of stimulation. While at low concentrations of DEA/NO (0.5 µM) the effect of PDE1 and PDE2 inhibitors is additive, at maximal DEA/NO (5.0 µM) there is an apparent more than additive effect, such that the level of cGMP attained by the combined inhibitors is greater than the sum of the effect of each inhibitor alone.

What is claimed is:

1. A product comprising (a) PDE1 inhibitor (6aR,9aS)-5,6a,7,8,9,9a-hexahydro-5-methyl-3-(phenylamino)-2-((4-Pyridin-2yl)-benzyl)-cyclopent[4,5]imidazo[1,2-a]pyrazolo[4,3-e]pyrimidin-4(2H)-one, in free or salt form, and (b) PDE2 inhibitor 2-(3,4-Dimethoxybenzyl)-7-{(1R)-1-[(1R)-1-hydroxyethyl]-4-phenylbutyl}-5-methylimidazo[5,1-f][1,2,4]triazin-4(3H)-one (BAY 60-7550), in free or salt form.

2. A pharmaceutical composition comprising PDE1 inhibitor, (6aR,9aS)-5,6a,7,8,9,9a-hexahydro-5-methyl-3-(phenylamino)-2-((4-Pyridin-2yl)-benzyl)-cyclopent[4,5]imidazo[1,2-a]pyrazolo[4,3-e]pyrimidin-4(2H)-one, in free or pharmaceutically acceptable salt form, and PDE2 inhibitor 2-(3,4-Dimethoxybenzyl)-7-{(1R)-1-[(1R)-1-hydroxyethyl]-4-phenylbutyl}-5-methylimidazo[5,1-f][1,2,4]triazin-4(3H)-one (BAY 60-7550), in free or pharmaceutically acceptable salt form, in admixture with a pharmaceutically acceptable diluent or carrier.

3. The pharmaceutical composition according to claim 2, wherein the composition is a fixed pharmaceutical composition wherein the PDE1 and PDE2 therapeutic agents are in a single dosage form.

4. The pharmaceutical composition according to claim 2, wherein the composition is a free pharmaceutical composition, wherein the PDE1 and PDE2 therapeutic agents are in a separate dosage form.

5. The pharmaceutical composition according to claim 2, wherein the PDE1 inhibitor and PDE2 inhibitor, in free or ophthalmologically acceptable salt form is in combination or association with an ophthalmologically acceptable diluent or carrier.

6. A method of treating any of the following conditions: Parkinson's disease, restless leg tremors, dyskinesias, Huntington's disease, Alzheimer's disease, drug-induced movement disorders, depression, attention deficit disorder, attention deficit hyperactivity disorder, bipolar illness, anxiety, sleep disorder, narcolepsy, cognitive impairment, dementia, Tourette's syndrome, autism, fragile X syndrome, psychostimulant withdrawal, drug addiction, cerebrovascular disease, stroke, congestive heart disease, hypertension, pulmonary hypertension, pulmonary arterial hypertension, sexual dysfunction, asthma, chronic obstructive pulmonary disease, allergic rhinitis, autoimmune and inflammatory diseases; female sexual dysfunction, exercise amenorrhoea, anovulation, menopause, menopausal symptoms, pre-menstrual syndrome, premature labor, infertility, irregular menstrual cycles, abnormal uterine bleeding, osteoporosis, multiple sclerosis, prostate enlargement, prostate cancer, hypothyroidism, estrogen-induced endometrial hyperplasia or carcinoma, glaucoma or elevated intraocular pressure, psychosis, psychotic symptoms, hallucinations, paranoid or bizarre delusions, or disorganized speech and thinking, schizophrenia, schizoaffective disorder, schizophreniform disorder, psychotic disorder, delusional disorder, mania in acute manic episodes and bipolar disorder, or traumatic brain injury, comprising administering an effective amount of the pharmaceutical composition according to claim 4, to a patient in need of such treatment, wherein treatment excludes prophylaxis.

7. The method of claim 6, wherein the condition is selected from the group consisting of Parkinson's disease, schizophrenia, narcolepsy, glaucoma, female sexual dysfunction, cognitive disorder, anxiety and depression.

8. The pharmaceutical composition according to claim 2 for use in the treatment Parkinson's disease, restless leg tremors, dyskinesias, Huntington's disease, Alzheimer's disease, drug-induced movement disorders, depression, attention deficit disorder, attention deficit hyperactivity disorder, bipolar illness, anxiety, sleep disorder, narcolepsy, cognitive impairment, dementia, Tourette's syndrome, autism, fragile X syndrome, psychostimulant withdrawal, drug addiction, cerebrovascular disease, stroke, congestive heart disease, hypertension, pulmonary hypertension, pulmonary arterial hypertension, sexual dysfunction, asthma, chronic obstructive pulmonary disease, allergic rhinitis, autoimmune and inflammatory diseases; female sexual dysfunction, exercise amenorrhoea, anovulation, menopause, menopausal symptoms, pre-menstrual syndrome, premature labor, infertility, irregular menstrual cycles, abnormal uterine bleeding, osteoporosis, multiple sclerosis, prostate enlargement, prostate cancer, hypothyroidism, estrogen-induced endometrial hyperplasia or carcinoma, glaucoma or elevated intraocular pressure, psychosis, psychotic symptoms, hallucinations, paranoid or bizarre delusions, or disorganized speech and thinking, schizophrenia, schizoaffective disorder, schizophreniform disorder, psychotic disorder, delusional disorder, mania in acute manic episodes and bipolar disorder, or traumatic brain injury, wherein treatment excludes prophylaxis.

9. A method of treating any of the following conditions: Parkinson's disease, restless leg tremors, dyskinesias, Huntington's disease, Alzheimer's disease, drug-induced movement disorders, depression, attention deficit disorder, attention deficit hyperactivity disorder, bipolar illness, anxiety, sleep disorder, narcolepsy, cognitive impairment, dementia, Tourette's syndrome, autism, fragile X syndrome, psychostimulant withdrawal, drug addiction, cerebrovascular disease, stroke, congestive heart disease, hypertension, pulmonary hypertension, pulmonary arterial hypertension, sexual dysfunction, asthma, chronic obstructive pulmonary disease, allergic rhinitis, autoimmune and inflammatory diseases; female sexual dysfunction, exercise amenorrhoea, anovulation, menopause, menopausal symptoms, pre-menstrual syndrome, premature labor, infertility, irregular menstrual cycles, abnormal uterine bleeding, osteoporosis, multiple sclerosis, prostate enlargement, prostate cancer, hypothyroidism, estrogen-induced endometrial hyperplasia or carcinoma, glaucoma or elevated intraocular pressure, psychosis, psychotic symptoms, hallucinations, paranoid or bizarre delusions, or disorganized speech and thinking, schizophrenia, schizoaffective disorder, schizophreniform disorder, psychotic disorder, delusional disorder, mania in acute manic episodes and bipolar disorder, traumatic brain injury; comprising administering an effective amount of (a) PDE1 inhibitor, (6aR,9aS)-5,6a,7,8,9,9a-hexahydro-5-methyl-3-(phenylamino)-2-((4-Pyridin-2yl)-benzyl)-cyclopent[4,5]imidazo[1,2-a]pyrazolo[4,3-e]pyrimidin-4(2H)-one, in free or pharmaceutically acceptable salt form, and (b) PDE2 inhibitor 2-(3,4-Dimethoxybenzyl)-7-{(1R)-1-[(1R)-1-hydroxyethyl]-4-phenylbutyl}-5-methylimidazo[5,1-f][1,2,4]triazin-4(3H)-one (BAY 60-7550), in free or pharmaceutically acceptable salt form, to a patient in need of such treatment, wherein treatment excludes prophylaxis.

10. The method of claim 9, wherein the condition is selected from the group consisting of Parkinson's disease, schizophrenia, narcolepsy, glaucoma, female sexual dysfunction, cognitive disorder, anxiety and depression.

* * * * *